(12) United States Patent
Endo et al.

(10) Patent No.: US 9,597,011 B2
(45) Date of Patent: Mar. 21, 2017

(54) RESPIRATORY PHASE DETERMINATION APPARATUS, RESPIRATORY PHASE DETERMINATION METHOD AND RESPIRATORY PHASE DETERMINATION PROGRAM

(71) Applicant: PANASONIC CORPORATION, Osaka (JP)

(72) Inventors: Mitsuru Endo, Osaka (JP); Noriaki Horii, Kyoto (JP); Maki Yamada, Kanagawa (JP)

(73) Assignee: PANASONIC CORPORATION, Osaka (JP)

( * ) Notice: Subject to any disclaimer, the term of this patent is extended or adjusted under 35 U.S.C. 154(b) by 0 days.

(21) Appl. No.: 14/266,187

(22) Filed: Apr. 30, 2014

(65) Prior Publication Data

US 2014/0243697 A1    Aug. 28, 2014

Related U.S. Application Data

(63) Continuation of application No. PCT/JP2013/005775, filed on Sep. 27, 2013.

(30) Foreign Application Priority Data

Dec. 28, 2012   (JP) .................. 2012-287619

(51) Int. Cl.
*A61B 5/08*    (2006.01)
*A61B 7/00*    (2006.01)
*A61B 5/087*   (2006.01)

(52) U.S. Cl.
CPC ............ *A61B 5/0816* (2013.01); *A61B 7/003* (2013.01); *A61B 5/087* (2013.01); *A61B 2562/0204* (2013.01)

(58) Field of Classification Search
CPC .............................. A61B 5/0816; A61B 7/003
(Continued)

(56) References Cited

U.S. PATENT DOCUMENTS 6,168,568 B1 *  1/2001  Gavriely .................. 600/529
6,261,238 B1    7/2001  Gavriely
(Continued)

FOREIGN PATENT DOCUMENTS

CN    102149317 A    8/2011
CN    102395322 A    3/2012
(Continued)

OTHER PUBLICATIONS

Moussavi, et al. "Automated Detection of Respiratory Phases by Acoustical Means." International Conference of the IEEE Engineering in Medicine and Biology Society. 1998. 20(1):21-4.*
(Continued)

*Primary Examiner* — Tiffany Weston
(74) *Attorney, Agent, or Firm* — Greenblum & Bernstein, P.L.C.

(57) ABSTRACT

Disclosed is a respiratory phase determination apparatus enabling a respiratory phase determination robust to personal differences in respiration among subjects and fluctuations in respiration of subjects in person without any need for calibration. The apparatus includes a first period feature value extraction section that extracts a first period feature value representing a feature of a first breath sound in a respiratory period, a second period feature value extraction section that extracts a second period feature value representing a feature of a second breath sound in the respiratory period, a feature value relativization/combining section that relativizes the first and the second period feature values and calculates a combined feature value, and a respiratory phase determination section that compares combined feature val-
(Continued)

ues of two neighboring respiratory periods and determines whether the two respiratory periods are each an inspiratory phase or expiratory phase based on the comparison result and a predetermined datum.

8 Claims, 6 Drawing Sheets

(58) Field of Classification Search
USPC .................................................. 600/529–534
See application file for complete search history.

(56) References Cited

U.S. PATENT DOCUMENTS

| 2003/0212303 | A1* | 11/2003 | Kahn ................................ 600/3 |
| 2005/0182337 | A1 | 8/2005 | Botbol et al. |
| 2010/0210962 | A1* | 8/2010 | Xu et al. ....................... 600/529 |
| 2010/0262031 | A1 | 10/2010 | Fu et al. |
| 2011/0034818 | A1 | 2/2011 | Gat et al. |
| 2012/0283598 | A1 | 11/2012 | Horii et al. |

FOREIGN PATENT DOCUMENTS

| EP | 2471461 | | 7/2012 |
| JP | 2001-505085 | A | 4/2001 |
| JP | 2011-519289 | A | 7/2011 |
| JP | 2012-523249 | A | 10/2012 |
| WO | 2012/060107 | A1 | 5/2012 |

OTHER PUBLICATIONS

Z. K. Moussavi et al., "Computerised acoustical respiratory phase detection without airflow measurement," Medical & Biological Engineering & Computing 2000 vol. 38, p. 198-p. 203.
Saiful Huq et al., "Acoustic breath-phase detection using tracheal breath sounds," Medical & Biological Engineering & Computing 2012 vol. 50, p. 297-p. 308.
International Search Report for Application No. PCT/JP2013/005775 dated Oct. 29, 2013.
Extended European Search Report issued in European Patent Application No. 13848112.2, mailed Feb. 9, 2016.

* cited by examiner

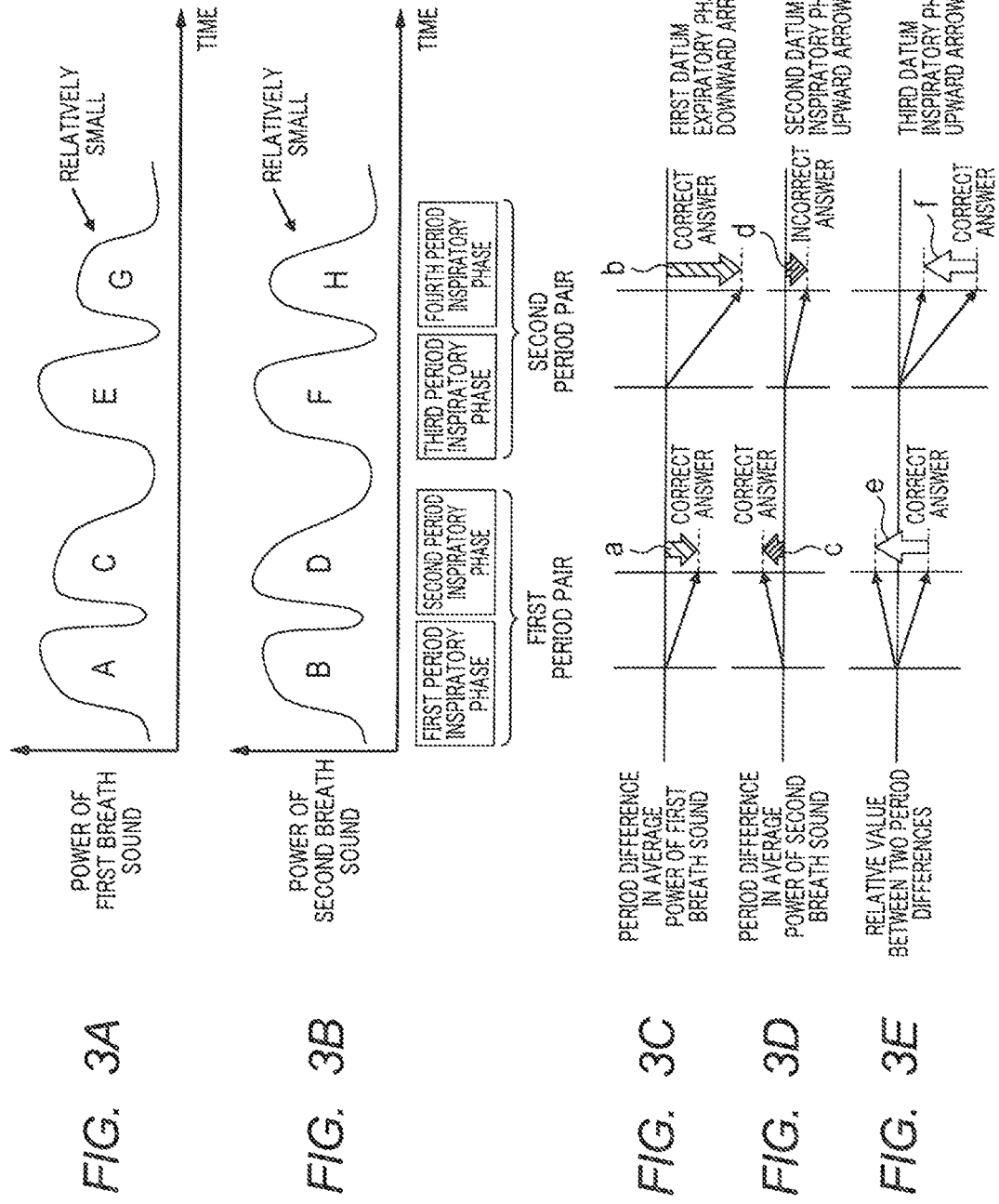

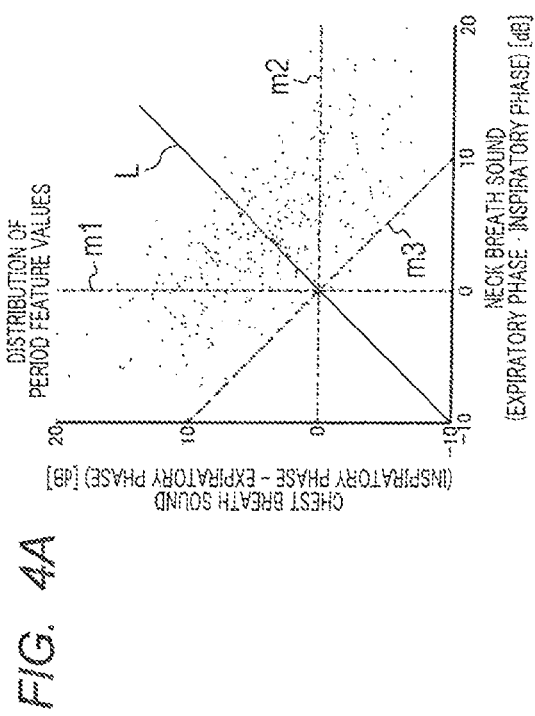
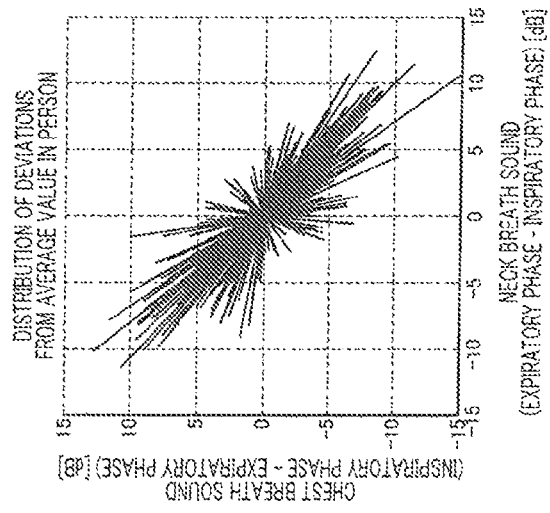
FIG. 4A
FIG. 4B
FIG. 4C

RESPIRATORY PHASE DETERMINATION APPARATUS, RESPIRATORY PHASE DETERMINATION METHOD AND RESPIRATORY PHASE DETERMINATION PROGRAM

TECHNICAL FIELD

The present invention relates to a respiratory phase determination apparatus, a respiratory phase determination method and a respiratory phase determination program for determining a respiratory phase based on a breath sound.

BACKGROUND ART

Heretofore, respiratory phase determination apparatuses are known which determine a respiratory phase based on a breath sound of an animal that performs pulmonary respiration. A breath sound is a sound generated as a result of respiration. A respiratory phase includes an inspiratory phase in which the air is taken into the lung and an expiratory phase in which the air is discharged from the lung, and these two phases are normally alternately repeated. Note that the respiratory phase determination apparatuses are used, for example, for lung sound analysis apparatuses for asthma-related tests.

A common operation of a respiratory phase determination apparatus is as follows. The respiratory phase determination apparatus first extracts a respiratory periods each divided by a pause between inspiration and expiration from a breath sound of a person to be measured (hereinafter referred to as "subject"), and feature values. The respiratory phase determination apparatus determines whether a respiratory period is an inspiratory phase (also referred to as "inspiration period") or expiratory phase (also referred to as "expiration period") depending on whether or not the feature value meets a predetermined datum (conditional expression). This determination is referred to as "respiratory phase determination" hereinafter.

The above-described feature values can be roughly divided into the following three categories.

A feature value using the magnitude of power or amplitude as a datum belongs to the first category. As such feature values, for example, power of a breath sound of the chest (NPL 1), power of a breath sound of the neck (PTL 1, NPL 2), and maximum amplitude of a breath sound of the neck (PTL 1) or the like are known.

A feature value using the length of a respiratory period as a datum belongs to the second category. As such feature values, for example, length of a respiratory period (PTL 1, NPL 2), ½ Gaussian width (PTL 1) are known.

A feature value using the rate of change of power in a short time as a datum belongs to the third category. As such feature values, for example, power in the first-half part of a breath sound of the neck (NPL 2), difference in power between the first ⅓ part and the last ⅓ part of a breath sound of the neck (NPL 2), angle of inclination at a rising edge (PTL 1), and angle of inclination at a falling edge (PTL 1, NPL 2) are known.

CITATION LIST

Patent Literature

PTL 1
US Patent Application Publication No. 2010-0262031

Non-Patent Literature

NPL 1
Z. K. Moussavi et al., "Computerised acoustical respiratory phase detection without airflow measurement," Medical & Biological Engineering & Computing 2000 Vol. 38, P198-P203

NPL 2
Saiful Huq et al., "Acoustic breath-phase detection using tracheal breath sounds," Medical & Biological Engineering & Computing 2012 Vol. 50, P297-P308

SUMMARY OF INVENTION

Technical Problem

However, since the respiratory phase determination apparatuses according to NPLs 1 and 2 perform respiratory phase determination based on a feature value extracted from one of the breath sound of the neck and the breath sound of the chest, there may be non-conformance to a datum due to personal differences in respiration between subjects or there may be a deviation from a datum due to a personal variation in respiration of a subject. This results in a problem of lack of robustness in the determination.

On the other hand, as a counter measure for the problem with non-conformance to the datum due to personal differences in respiration between subjects, a technique is known which adjusts the datum for a subject through calibration. For example, the respiratory phase determination apparatus of PTL 1 gives an instruction signal by a subject in person to part of measured data and selects a datum that better fits the subject in person from among a plurality of datums. However, such calibration has a problem of taking time and effort.

An object of the present invention is to provide a respiratory phase determination apparatus, a respiratory phase determination method and a respiratory phase determination program robust to personal differences in respiration among subjects or variations in respiration of subjects in person and capable of making a respiratory phase determination without any need for calibration.

Solution to Problem

A respiratory phase determination apparatus according to an aspect of the present invention includes: a respiratory period estimation section that estimates a respiratory period based on at least one of a first breath sound acquired from a first position of a body of a subject and a second breath sound acquired in synchronization with the first breath sound from a second position of the body of the subject; a first period feature value extraction section that extracts a first period feature value representing a feature of the first breath sound in the respiratory period; a second period feature value extraction section that extracts a second period feature value representing a feature of the second breath sound in the respiratory period; a feature value relativization/combining section that relativizes the first period feature value and the second period feature value and calculates a combined feature value; and a respiratory phase determination section that compares the combined feature value in the respiratory period with a combined feature value in a respiratory period near the respiratory period and determines whether each of the two respiratory periods is an inspiratory phase or expiratory phase based on a comparison result and a predetermined datum.

A respiratory phase determination method according to an aspect of the present invention includes: estimating a respiratory period based on at least one of a first breath sound acquired from a first position of a body of a subject and a second breath sound acquired in synchronization with the first breath sound from a second position of the body of the subject; extracting a first period feature value representing a feature of the first breath sound in the respiratory period; extracting a second period feature value representing a feature of the second breath sound in the respiratory period; relativizing the first period feature value and the second period feature value and calculating a combined feature value; and comparing the combined feature value in the respiratory period with a combined feature value in a respiratory period near the respiratory period and determining whether each of the two respiratory periods is an inspiratory phase or expiratory phase based on a comparison result and a predetermined datum.

A respiratory phase determination program according to an aspect of the present invention is a program that causes a computer to execute processing including: estimating a respiratory period based on at least one of a first breath sound acquired from a first position of a body of a subject and a second breath sound acquired in synchronization with the first breath sound from a second position of the body of the subject; extracting a first period feature value representing a feature of the first breath sound in the respiratory period; extracting a second period feature value representing a feature of the second breath sound in the respiratory period; relativizing the first period feature value and the second period feature value and calculating a combined feature value; and comparing the combined feature value in the respiratory period with a combined feature value in a respiratory period near the respiratory period and determining whether each of the two respiratory periods is an inspiratory phase or expiratory phase based on a comparison result and a predetermined datum.

Advantageous Effects of Invention

According to the present invention, it is possible to make a respiratory phase determination robust to personal differences in respiration among subjects and variations in respiration of subjects in person without any need for calibration.

BRIEF DESCRIPTION OF DRAWINGS

FIGS. 3A to 3E illustrate principles of operation of improving robustness of the respiratory phase determination apparatus according to the embodiment of the present invention;

FIGS. 4A to 4C illustrate a data distribution for improving robustness of the respiratory phase determination apparatus according to the embodiment of the present invention;

DESCRIPTION OF EMBODIMENT

Hereinafter, an embodiment of the present invention will be described in detail with reference to the accompanying drawings.

<Configuration of Respiratory Phase Determination Apparatus>

Figure 1:
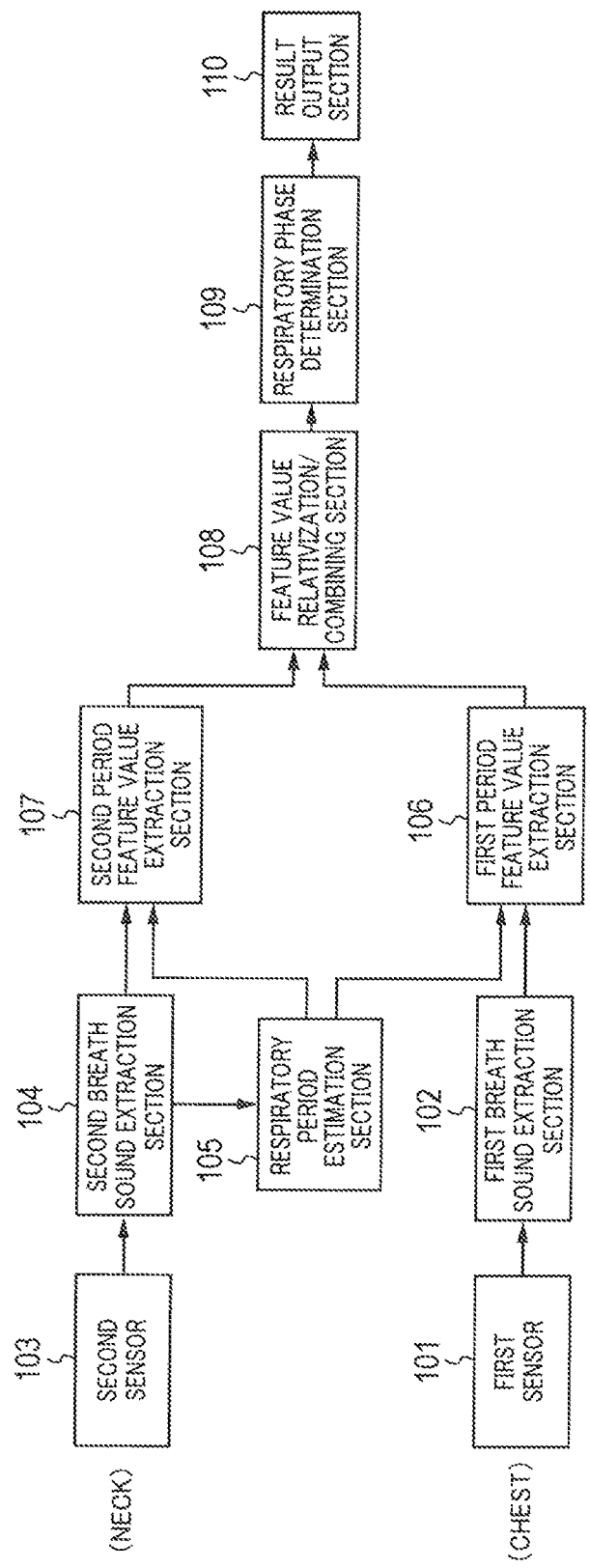
FIG. 1 is a block diagram illustrating a configuration example of a respiratory phase determination apparatus according to an embodiment of the present invention.

First, a configuration of a respiratory phase determination apparatus according to an embodiment of the present invention will be described. FIG. 1 is a block diagram illustrating a configuration example of the respiratory phase determination apparatus according to the present embodiment.

In FIG. 1, the respiratory phase determination apparatus includes first sensor 101, first breath sound extraction section 102, second sensor 103, second breath sound extraction section 104, respiratory period estimation section 105, first period feature value extraction section 106, second period feature value extraction section 107, feature value relativization/combining section 108, respiratory phase determination section 109, and result output section 110. In the present embodiment, first sensor 101 and second sensor 103 acquire different biological sounds. Therefore, a biological sound acquired by first sensor 101 is called "first biological sound." A breath sound included in the first biological sound is called "first breath sound." Likewise, a biological sound acquired by second sensor 103 is called "second biological sound." A breath sound included in the second biological sound is called "second breath sound."

First sensor 101 is a sensor that acquires a first biological sound including a first breath sound from a subject. First sensor 101 is attached to a range of the body of the subject (an example of a first position) in which a vesicular breath sound can be acquired. This range is, for example, predetermined positions of the chest or back where a vesicular breath sound is heard in addition to the second intercostal space on the right midclavicular line or third intercostal space on the right midclavicular line. First sensor 101 notifies first breath sound extraction section 102 of the acquired first biological sound.

First breath sound extraction section 102 extracts a first breath sound from the first biological sound using a bandpass filter. The first breath sound constitutes a power pattern. First breath sound extraction section 102 then notifies first period feature value extraction section 106 of the extracted first breath sound.

Second sensor 103 is a sensor that acquires a second biological sound including a second breath sound from the same subject in synchronization with the acquisition of the aforementioned first biological sound. Second sensor 103 is attached to a range of the body of the subject where a tracheal breath sound or bronchial breath sound can be acquired (an example of a second position). This range is, for example, predetermined positions of the chest or back where a tracheal breath sound or bronchial breath sound is heard in addition to the upper cervical trachea or the second intercostal space on the right side of the sternum. Second sensor 103 notifies second breath sound extraction section 104 of the acquired second biological sound.

Second breath sound extraction section 104 extracts a second breath sound from the second biological sound using a band-pass filter. The second breath sound constitutes a power pattern. Second breath sound extraction section 104 notifies respiratory period estimation section 105 and second period feature value extraction section 107 of the extracted second breath sound.

Respiratory period estimation section 105 estimates a respiratory period based on the power pattern of the second breath sound. The respiratory period is a period divided by a pause (pause frame which will be described later) between inspiration and expiration as described above. The term "pause" herein is not limited to a pause between inspiration and expiration. More specifically, not only a pause between inspiration and expiration, but also a pause between expiration and inspiration is extracted as a pause, i.e., a pause is extracted regardless of the sequence of inspiration and expiration. A power pattern of one respiratory period takes, for example, a mountain shape and corresponds to one of an inspiratory phase and an expiratory phase. Respiratory period estimation section 105 notifies first period feature value extraction section 106 and second period feature value extraction section 107 of the estimated respiratory period.

First period feature value extraction section 106 calculates average power of the first breath sound for each respiratory period. This average power is called a first period feature value. A power pattern of one respiratory period is divided into a plurality of frames (one frame corresponds to a short period of time of 20 ms or the like). The average power has a value obtained by averaging power in frame units. First period feature value extraction section 106 then notifies feature value relativization/combining section 108 of the calculated first period feature value.

Second period feature value extraction section 107 calculates average power of the second breath sound for each respiratory period. This average power is called a second period feature value. Second period feature value extraction section 107 then notifies feature value relativization/combining section 108 of the calculated second period feature value.

Feature value relativization/combining section 108 relativizes the first period feature value and the second period feature value, and combines the feature values. That is, feature value relativization/combining section 108 subtracts the first period feature value from the second period feature value in decibel units and calculates a combined feature value. Feature value relativization/combining section 108 then notifies respiratory phase determination section 109 of the calculated combined feature value.

Respiratory phase determination section 109 compares combined feature values in two respiratory periods located close to each other (e.g., neighboring positions). Respiratory phase determination section 109 determines whether each respiratory period is an expiratory phase or inspiratory phase based on the comparison result and a predetermined datum. For example, respiratory phase determination section 109 determines the respiratory period of a greater combined feature value to be an expiratory phase and determines the respiratory period of a smaller combined feature value to be an inspiratory phase. Respiratory phase determination section 109 then notifies result output section 110 of the determination result.

Result output section 110 outputs the determination result using a predetermined method (e.g., file output or screen display).

The description of the configuration of the respiratory phase determination apparatus according to the present embodiment has been given thus far.

<Operation of Respiratory Phase Determination Apparatus>

Figure 2:
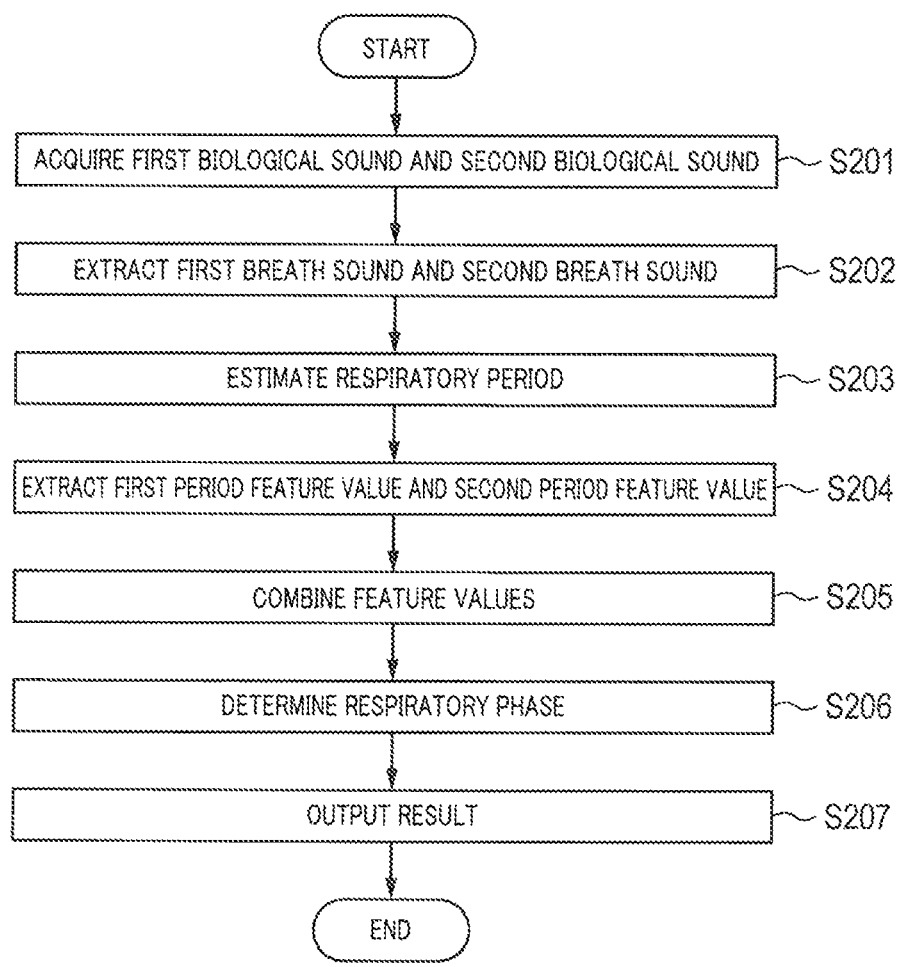
FIG. 2 is a flowchart illustrating an operation example of the respiratory phase determination apparatus according to the embodiment of the present invention.

Next, an operation example of the respiratory phase determination apparatus according to the present embodiment will be described. FIG. 2 is a flowchart illustrating an operation example of the respiratory phase determination apparatus according to the present embodiment.

In step S201, first sensor 101 acquires a first biological sound of a subject. Second sensor 103 acquires a second biological sound from the same subject. The first biological sound and the second biological sound include sounds deriving from a living body such as cardiac sound and muscle sound as well as breath sounds, or also include external noise.

In step S202, first breath sound extraction section 102 extracts a first breath sound from the first biological sound using a band-pass filter. Second breath sound extraction section 104 extracts a second breath sound from the second biological sound using a band-pass filter. The band-pass filter is used to remove a cardiac sound or noise in a high-frequency region.

In step S203, respiratory period estimation section 105 estimates a respiratory period based on a power pattern of the second breath sound. This operation will be more specifically described as follows. First, respiratory period estimation section 105 extracts a frame that falls below a predetermined threshold (hereinafter, referred to as "pause frame") from among frames into which the power pattern of the second breath sound has been divided. Respiratory period estimation section 105 then determines periods during which frames other than the pause frame continue to be respiratory period candidates. Respiratory period estimation section 105 then determines and excludes respiratory period candidates shorter than a predetermined length as noise and estimates the remaining candidates as respiratory periods. The estimated respiratory period has, for example, a mountain type power pattern. Respiratory period estimation section 105 may divide the estimated respiratory periods which are longer than the predetermined length or may combine the estimated respiratory periods which are shorter than the predetermined length.

Note that respiratory periods estimated from the second breath sound is more advantageous from the standpoint of a dynamic range, but may also be estimated from the first breath sound or may also be estimated using both the first breath sound and the second breath sound. The respiratory period estimated from the second breath sound and the respiratory period estimated from the first breath sound are synchronized with the respiration operation, and thus both respiratory periods generally match.

In step S204, first period feature value extraction section 106 extracts a first period feature value in the estimated respiratory period. Second period feature value extraction section 107 extracts a second period feature value in the estimated respiratory period. The first period feature value is, for example, average power of the first breath sound in the estimated respiratory period. The second period feature value is, for example, average power of the second breath sound in the estimated respiratory period.

The average power may be calculated without using all frames in the respiratory period to increase reliability of a period feature value. For example, first period feature value extraction section 106 and second period feature value extraction section 107 may narrow down the respiratory period to higher 50% or higher 20% band power periods of the respiratory periods and calculate the average power based on the frames in those periods. For example, first period feature value extraction section 106 and second period feature value extraction section 107 may exclude considerably fluctuating portions among acoustic analysis frames through outlier handling to reduce noise within a pass-band.

In step S205, feature value relativization/combining section 108 combines the first period feature value and the second period feature value. That is, feature value relativization/combining section 108 subtracts the first period feature value from the second period feature value and determines the result to be a combined feature value. The first period feature value is a vesicular breath sound whose inspiratory phase tends to have a greater sound than the expiratory phase (hereinafter, referred to as "first datum"). On the other hand, the second period feature value is a tracheal breath sound or bronchial breath sound whose expiratory phase tends to have a greater sound than the inspiratory phase (hereinafter, referred to as "second datum"). On the other hand, the first period feature value and the second period feature value simultaneously increase or decrease, and therefore have high correlation, and if a breath sound of one period happens to be small due to irregularities, both the first period feature value and the second period feature value simultaneously decrease. Therefore, if a difference between the two period feature values is calculated (the first period feature value is subtracted from the second period feature value), the datum has a reverse sign, and it is therefore expected that an average margin is added to the datum of the combined period feature value and fluctuations due to the irregularities are cancelled out. This point will be described in further detail later.

In step S206, respiratory phase determination section 109 makes a respiratory phase determination. The operation of this respiratory phase determination is as follows. First, respiratory phase determination section 109 compares combined feature values in two respiratory periods located close to each other. That is, respiratory phase determination section 109 compares a combined feature value in a predetermined respiratory period with a combined feature value in a respiratory period in the vicinity of the respiratory period (e.g., neighboring period). Respiratory phase determination section 109 then determines whether each respiratory period is an expiratory phase or an inspiratory phase based on the comparison result and a predetermined datum. Here, the respiratory phase determination is made for each pair of respiratory periods. However, in normal respiration, a ventilation air volume of preceding inspiration substantially matches a ventilation air volume of the following expiration. Thus, the pair is preferably selected ex post facto so that a pair of respiratory periods arranged in order of inspiration first and then expiration is extracted.

In step S207, result output section 110 outputs the respiratory phase determination result. In this result output, for example, the start/end of respiratory period and the type of respiratory phase may be outputted to a file or graphically outputted to a display. Alternatively, result output section 110 may output the result of a breath sound analysis conducted in accordance with a respiratory phase based on the respiratory phase determination result.

The overall flow has been described above. However, the basic time unit of processing differs from one step to another. Step S201 is done in block units of AD conversion. Steps S202 and S203 are done in frame units of acoustic analysis processing. Furthermore, steps S204 and S205 are done in estimated respiratory period units. Steps S206 and S207 are processing done over a plurality of respiratory periods. The respective steps are combined as pipeline processing.

The description of the operation of the respiratory phase determination apparatus according to the present embodiment has been described thus far.

Next, features of the respiratory phase determination apparatus according to the embodiment of the present invention will be described in further detail using FIG. 3A to FIG. 5.

First, FIGS. 3A to 3E will be described. FIGS. 3A to 3E illustrate principles under which the respiratory phase determination apparatus according to the present embodiment achieves operation of improving robustness.

FIG. 3A illustrates a time series of power of the first breath sound in a power pattern. FIG. 3B illustrates a time series of power of the second breath sound in a power pattern. As shown in FIG. 3A and FIG. 3B, power of the first breath sound and power of the second breath sound each show mountain shape power patterns in four respiratory periods (hereinafter referred to as "periods"); first to fourth periods. In FIG. 3A, power pattern A shows power of the first breath sound in the first period, power pattern C shows power of the first breath sound in the second period, power pattern E shows power of the first breath sound in the third period and power pattern G shows power of the first breath sound in the fourth period. On the other hand, in FIG. 3B, power pattern B shows power of the second breath sound in the first period, power pattern D shows power of the second breath sound in the second period, power pattern F shows power of the second breath sound in the third period and power pattern H shows power of the second breath sound in the fourth period. It is assumed that the first period is an inspiratory phase, the second period is an expiratory phase, the third period is an inspiratory phase, and the fourth period is an expiratory phase. Since the first two periods; the first period and second period are adjacent to each other, they are called "first period pair." The first period pair represents a normal respiration pattern. Since the next two periods; the third period and fourth period are adjacent to each other, they are called "second period pair." The second period pair represents an irregular respiration pattern in which the fourth period is relatively small.

FIG. 3C illustrates a period difference of average power of the first breath sound. The period difference of average power is a difference in period feature values between two periods. Period difference "a" indicated by a downward arrow is a difference between average power of power pattern C (an example of the first period feature value) and average power of power pattern A (an example of first period feature value). Note that the average power of power pattern C is a value obtained by dividing power pattern C into a plurality of frames and averaging power of each frame as described above. Likewise, average power of power pattern A is a value obtained by dividing power pattern A into a plurality of frames and averaging power of each frame as described above. Period difference b indicated by a downward arrow is a difference between average power of power pattern G (an example of the first period feature value) and average power of power pattern E (an example of first period feature value). Note that the average power of power pattern G is a value obtained by dividing power pattern G into a plurality of frames and averaging power of each frame as described above. Likewise, average power of power pattern E is a value obtained by dividing power pattern E into a plurality of frames and averaging power of each frame as described above.

In FIG. 3C, since the arrow of period difference a is oriented a downward (negative) direction, average power of the second period (power pattern C) is smaller than average power of the first period (power pattern A). According to the first datum (expiratory phase<inspiratory phase, that is, it is the inspiratory phase that has greater average power), it is determined that the first period is the inspiratory phase and the second period is the expiratory phase. According to the first datum (downward arrow is a correct answer), the determination result is correct. Likewise, in FIG. 3C, since the arrow of period difference b indicates a downward direction, average power of the fourth period (power pattern G) is smaller than average power of the third period (power pattern E). Thus, according to the first datum, it is determined that the third period is an inspiratory phase and the fourth period is an expiratory phase, and the determination result is correct.

FIG. 3D illustrates a period difference in average power of the second breath sound. Period difference c indicated by an upward arrow is a difference between average power of power pattern D (an example of the second period feature value) and average power of power pattern B (an example of the second period feature value). Period difference d indicated by a downward arrow is a difference between average power of power pattern H (an example of the second period feature value) and average power of power pattern F (an example of the second period feature value).

In FIG. 3D, since the arrow of period difference c indicates an upward (positive) direction, average power of the second period (power pattern D) is greater than average power of the first period (power pattern B). Thus, according to the second datum (inspiratory phase<expiratory phase, that is, it is the expiratory phase that has greater average power), it is determined that the first period is an inspiratory phase and the second period is an expiratory phase. According to the second datum (upward arrow is a correct answer), the determination result is correct. However, since the arrow of period difference d in FIG. 3D indicates a downward direction, average power of the fourth period (power pattern H) is smaller than average power of the third period (power pattern F). Thus, according to the second datum, it is determined that the third period is an expiratory phase and the fourth period is an inspiratory phase, and the determination result is an incorrect answer (error).

In this way, in FIG. 3D, in the first period and the second period which are normal respiration patterns, the respiratory phase is determined correctly, whereas in the third period and the fourth period which are irregular (when average power of the fourth period is relatively small) respiration patterns, the respiratory phase is not correctly determined. That is, when a respiratory phase determination is made based on only the period difference in the second period feature value, if there are irregular respiration patterns, there can be cases where correct determinations are not made. Thus, in the present embodiment, a respiratory phase determination is made based on a feature value obtained by combining the first breath sound feature value and the second breath sound feature value. This can prevent cases where correct determinations are not made in the cases of irregular respiration patterns. The details thereof will be described below with reference to FIG. 3E.

FIG. 3E illustrates a relative value between difference of average power of the first breath sound in a pair of periods and difference of average power of the second breath sound in a pair of periods. Relative value "e" indicated by an upward arrow is a relative value between period difference "a" and period difference "c". Relative value f indicated by an upward arrow is a relative value between period difference b and period difference d. In other words, relative value e can be said to be a period difference between the relative value between average power of power pattern B and average power of power pattern A (an example of the above-described combined feature value), and a relative value between average power of power pattern D and average power of power pattern C (an example of the above-described combined feature value). On the other hand, in other words, relative value f can be said to be a period difference between the relative value between average power of power pattern F and average power of power pattern E (an example of the above-described combined feature value), and a relative value between average power of power pattern H and average power of power pattern G (an example of the above-described combined feature value).

In FIG. 3E, regarding the first period pair, as shown by relative value e, the difference between average power of the second breath sound and average power of the first breath sound increases from the first period to the second period, and it is correctly determined that the first period is an inspiratory phase and the second period is an expiratory phase. In FIG. 3E, period difference "a" and period difference "c" are summed up into relative value "e", which is considered to enhance the datum making it less susceptible to personal differences.

In FIG. 3E, regarding the second period pair, as shown by relative value f, the fluctuation from the normal respiration pattern is substantially cancelled out and a stable period difference is obtained, which results in a correct answer. In this way, the system is considered to become robust to personal irregularities of respiration as well.

Next, FIGS. 4A to 4C will be described. FIGS. 4A to 4C illustrate a distribution of data for improving robustness of the respiratory phase determination apparatus according to the embodiment of the present invention.

Hereinafter, a verification conducted by inputting predetermined data to the respiratory phase determination apparatus of the present embodiment will be described with reference to FIGS. 4A to 4C. This input data represents breath sounds of 45 children recorded together with outputs of a respiration flow meter. In this input data, a respiratory period and a respiratory phase thereof (expiratory phase or respiratory phase) are defined from values of the respiration flow meter, and a preceding inspiration period and a following expiration period are combined as a pair.

FIG. 4A represents a distribution of period feature values. In FIG. 4A, values are plotted assuming a pair of inspiratory phase and expiratory phase as one point. In FIG. 4A, m1, m2 and m3 represent datum lines. The vertical axis shows a value obtained by subtracting an expiratory period power from an inspiratory period power of a chest breath sound as a first breath sound feature value. When this value is 0 or above, the feature value is applicable to the first datum. The horizontal axis shows a value obtained by subtracting the inspiratory period power from the expiratory period power of the tracheal breath sound as a second breath sound feature value. When this value is 0 or above, the feature value is applicable to the second datum. The number of points plotted in a region of 0 or less represents approximately 15% on both axes and those points result in errors with respect to each datum. Here, no point exists in the regions where values fall to 0 or below with respect to both datums. The respiratory phase determination apparatus of the present embodiment combines feature values along an axis L in a 45-degree direction of this FIG. 4A. Points on the right of and above the dotted line having a gradient of −1 which passes through the origin is applicable to the aforementioned third datum (see FIG. 3E). Since substantially no point is located on the left of and below the dotted line, it is clear that most period pairs are applicable to the third datum.

FIG. 4B represents a distribution of average margins of period feature values of subjects in person. In FIG. 4A, values are plotted by counting each period pair as one irrespective of subjects, whereas in FIG. 4B, an average value is obtained and plotted for each subject. A margin of each subject with respect to a datum can be known from the distance of each plotted point from a datum line (m1, m2, m3). When viewing from the vertical axis perspective points in the region of 0 or below represent subjects who are not applicable to the first datum due to individuality of feature values. On the other hand, When viewing from the horizontal axis perspective, points in the region of 0 or below represent subjects who are not applicable to the second datum due to individuality (personal difference) of feature values. When viewing FIG. 4B focusing on a 45-degree direction (axis L), it is clear that individualities of feature values combined by the respiratory phase determination apparatus of the present embodiment are shown and no subject failing to meet the datum is found in the verification data.

FIG. 4C represents a distribution of deviations from the average value of subjects in person. Assuming the average feature value is located at the origin for each subject, the difference between the value of each period pair and the average value of the subject in person is represented by a straight line from the origin. When a respiration pattern of a subject in person fluctuates, that is, when the breath sound of one respiratory phase relatively increases or decreases, this graph shows how the respiration pattern deviates in the feature value space, and shows that the distribution indicates a strong negative correlation. That is, the graph shows that although such a correlation may be considerably disadvantageous when one of the vertical axis and the horizontal axis is used as a datum, the respiration pattern is deviated in the direction nearly parallel to datum line m3 with respect to the third datum, and therefore such influences are reduced.

The robustness to personal differences in respiration among subjects and fluctuations in respiration of subjects in person verified as described above utilizes the nature of vesicular breath sound and tracheal breath sound. The following is an example of a case where improvement of robustness may not work out. For example, when vesicular breath sounds are recorded at two positions on the right and left and relativized equally, fluctuations corresponding to subjects in person can be canceled out. However, since the two datums are of the same type (inspiratory phase is larger in both cases), the average margin of a subject in person from whom a difference is calculated is distributed over positive and negative regions centered on 0.

Figure 5:
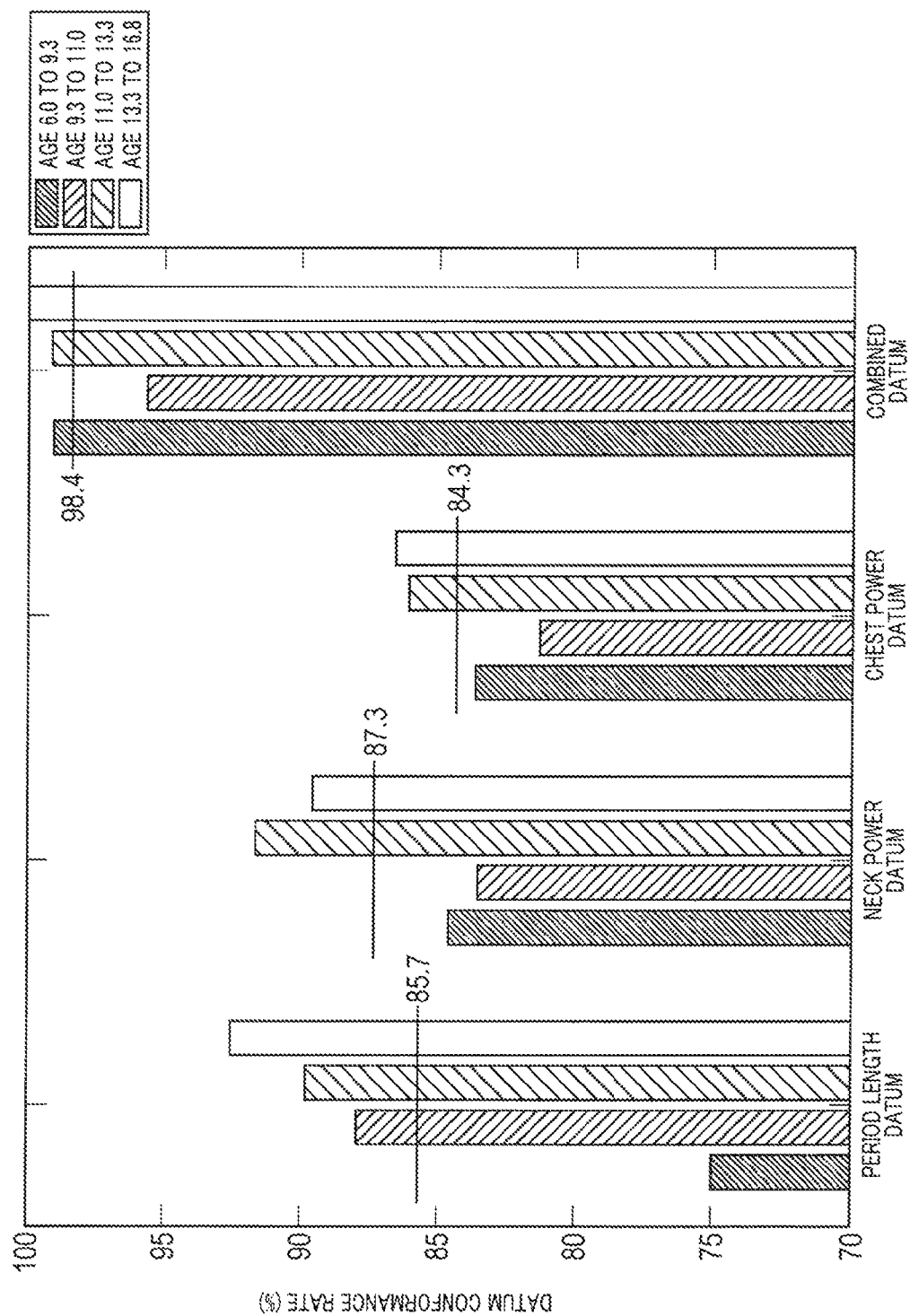
FIG. 5 illustrates results of performance evaluation using data of the respiratory phase determination apparatus according to the embodiment of the present invention.

Next, FIG. 5 will be described. FIG. 5 illustrates results of performance evaluation using data of the respiratory phase determination apparatus according to the embodiment of the present invention.

FIG. 5 shows results of examining the data-datum conformance rate for each period pair using the input data described in FIGS. 4A to 4C. There are four datums: period length datum, neck power datum, chest power datum, and combined datum from the left in FIG. 5. The period length datum is a datum that an expiratory phase has a greater period length than an inspiratory phase. The neck power datum is the aforementioned second datum and is a datum that an expiratory phase has greater power than an inspiratory phase. The chest power datum is the aforementioned first datum and is a datum that an inspiratory phase has greater power than an expiratory phase. The combined datum is the aforementioned third datum and is a datum that an expiratory phase has a greater relative value of neck power with respect to chest power than an inspiratory phase.

As shown in FIG. 5, the datum conformance rates of data as a whole were 85.7%, 87.3%, 84.3%, and 98.4% respectively. By combining (relativizing) the feature value corresponding to a conformance rate of 87.3% and the feature value corresponding to a conformance rate of 84.3%, the respiratory phase determination apparatus of the present embodiment significantly improved the conformance rate to 98.4%.

FIG. 5 also categorizes subjects into four equal parts in ascending order of age for the respective datums and shows datum conformance rates of respective age zones. Among the four datums, the period length datum in particular has high age dependency and it is observed that the datum conformance rate decreases as the age decreases. Though not so extreme as the period length datum, the neck power datum and the chest power datum also show that the datum conformance rate decreased as the age decreases. Thus, according to the period length datum, neck power datum, and chest power datum, the datum conformance rate decreased as the age decreases. In contrast, the combined datum obtained a high datum conformance rate irrespective of the age zone.

When a technique of determining a respiratory phase based on majority vote using a plurality of datums (e.g., technique in NPL 2) is applied, that is, when a respiratory phase is determined through decision by majority from the determination results based on the three datums: period length datum, neck power datum, and chest power datum respectively, the datum conformance rate was 94.3%. In contrast, when a respiratory phase determination was made based on the combined datum, the datum conformance rate was 98.4%. Therefore, using the combined datum as in the case of the respiratory phase determination apparatus of the present embodiment achieves a greater effect of improving robustness rather than covering non-conformance simply using a plurality of datums as in the case of the technique in NPL 2.

Thus, the respiratory phase determination apparatus according to the present embodiment extracts feature values from breath sounds at different positions of acquisition having the converse magnitude relationship between the inspiratory phase and the expiratory phase such as tracheal breath sound and vesicular breath sound, combines the two extracted feature values and makes a respiratory phase determination based on the combined feature value. In this way, the respiratory phase determination apparatus of the present embodiment can increase (add) a datum margin and reduce (cancel out) deviations of feature values due to irregularities. The increase in datum margin is robust to personal differences in respiration among subjects as shown in FIG. 4B. The reduction of deviations in feature values due to irregularities is robust to fluctuations in respiration of a subject in person as shown in FIG. 4C. Therefore, the respiratory phase determination apparatus according to the present embodiment is robust to personal differences in respiration among subjects and fluctuations in respiration of subjects in person, and can make a respiratory phase determination without any need for calibration.

Variations of Embodiment

The embodiment of the present invention has been described so far, but the above embodiment is merely an example and various modifications are possible. Variations of the embodiment will be described below.

For example, the respiratory phase determination apparatus of the present embodiment may adopt conflict handling which will be described below in addition to the aforementioned processing. Here, the necessity for conflict handling will be described. As described above, the base unit of respiratory phase determination is two respiratory periods. The respiratory phase determination apparatus makes a respiratory phase determination based on a magnitude relationship of feature values between the two respiratory periods. When the respiratory phase determination apparatus picks up the two respiratory periods consecutively, there may be a period pair beginning from an odd-numbered period and a period pair beginning from an even-numbered period. Upon making a respiratory phase determination on all these period pairs, the respiratory phase determination apparatus can obtain two determination results per period. In this case, there may be no problem if the two determination results match, but there may be a case where a conflict occurs in which the two determination results do not match. The processing to handle such a conflict is conflict handling which will be described below.

Figure 6A:
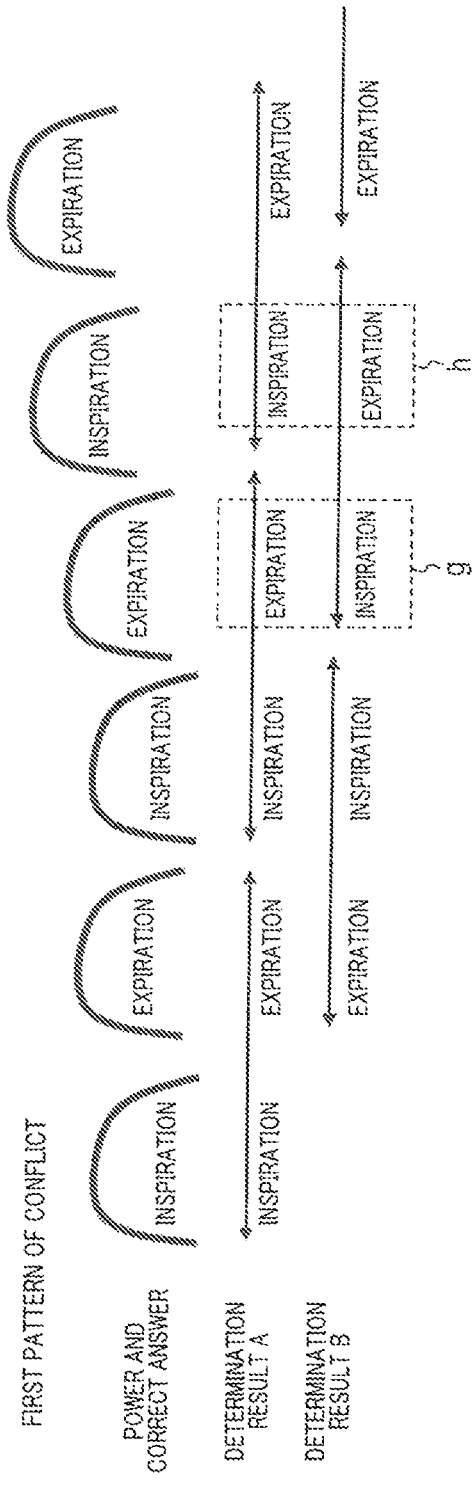
FIGS. 6A and 6B illustrate principles of operation of irregularity handling in periods of the respiratory phase determination apparatus according to the embodiment of the present invention.
Figure 6B:
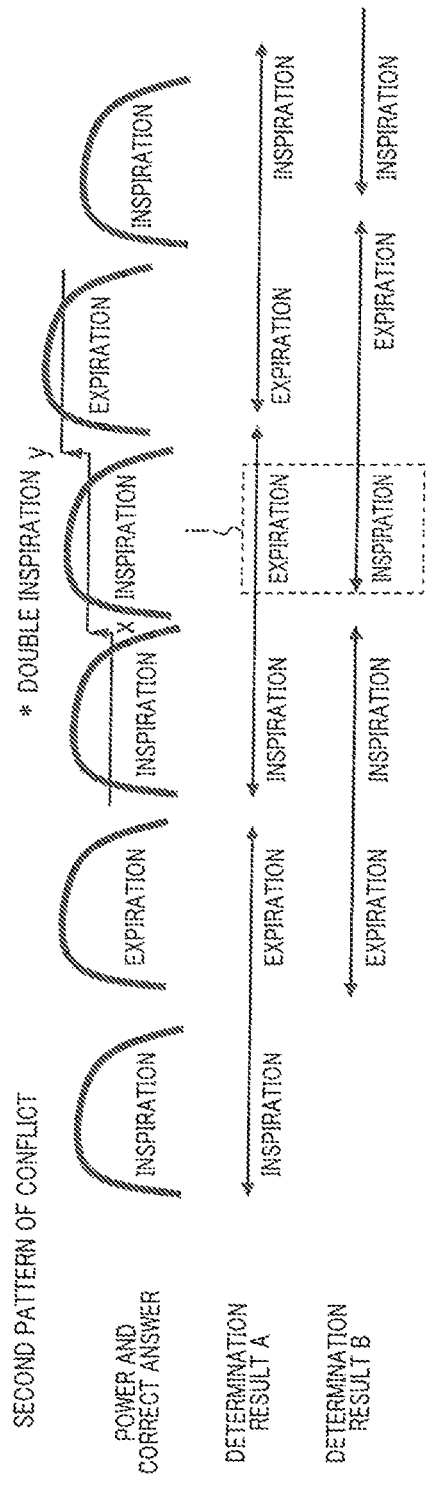

FIGS. 6A and 6B illustrate principles of operation of conflict handling carried out by the respiratory phase determination apparatus according to the embodiment of the present invention. The conflict handling is additionally performed by respiratory phase determination section 109 to make a respiratory phase determination (step S206 in FIG. 2).

FIG. 6A shows a first pattern of a conflict. In the example of FIG. 6A, conflicts (mismatch between determination result A and determination result B) occur at two consecutive locations shown by portions "g" and "h" enclosed by broken lines. In this case, respiratory phase determination section 109 leaves the determination result in which an inspiratory phase and an expiratory phase appear alternately as conflict handling in consideration of before portion "g" enclosed by a broken line and after portion "h" enclosed by a broken line. That is, in the case of pattern 1 in FIG. 6A, respiratory phase determination section 109 leaves determination result A.

FIG. 6B shows a second pattern of conflict. In the example of FIG. 6B, inspiratory phases appear consecutively due to irregularities of the respiration itself (* double inspiration), and a conflict (mismatch between determination result A and determination result B) occurs on portion "i" enclosed by a broken line. In this case, respiratory phase determination section 109 leaves the one having a greater difference (margin) from the datum as conflict handling. In other words, respiratory phase determination section 109 compares combined feature values (e.g., arrow x and arrow y) in period pairs including the period in which the conflict has occurred (portion "i" enclosed by a broken line) and leaves a determination result including a period pair having a greater combined feature value.

As described above, even when a conflict occurs in two determination results, the respiratory phase determination apparatus according to the embodiment of the present invention can obtain an appropriate determination result by performing conflict handling.

The embodiment and variations of the embodiment have been described with reference to a case where the present invention is implemented by hardware. However, the present invention can be implemented by software in concert with hardware.

A respiratory phase determination apparatus according this disclosure includes: a respiratory period estimation section that estimates a respiratory period based on at least one of a first breath sound acquired from a first position of a body of a subject and a second breath sound acquired in synchronization with the first breath sound from a second position of the body of the subject; a first period feature value extraction section that extracts a first period feature value representing a feature of the first breath sound in the respiratory period; a second period feature value extraction section that extracts a second period feature value representing a feature of the second breath sound in the respiratory period; a feature value relativization/combining section that relativizes the first period feature value and the second period feature value and calculates a combined feature value; and a respiratory phase determination section that compares the combined feature value in the respiratory period with a combined feature value in a respiratory period near the respiratory period and determines whether each of the two respiratory periods is an inspiratory phase or expiratory phase based on a comparison result and a predetermined datum.

In the respiratory phase determination apparatus according to this disclosure, the first breath sound and the second breath sound are breath sounds acquired at different positions where an inspiratory phase and expiratory phase have a reverse magnitude relation.

In the respiratory phase determination apparatus according to this disclosure, the respiratory phase determination section adopts a determination result with which inspiratory phases and expiratory phases appear alternately in a series of respiratory periods or adopts a determination result which has a greater difference from the datum, when two determination results for one respiratory period are obtained as a result of the determination, and are in conflict with each other.

The respiratory phase determination apparatus according to this disclosure further includes: a first sensor that is attached at the first position to acquire a first biological sound including the first breath sound; a second sensor that is attached at the second position to acquire a second biological sound including the second breath sound; a first breath sound extraction section that extracts the first breath sound from the first biological sound; and a second breath sound extraction section that extracts the second breath sound from the second biological sound.

The respiratory phase determination apparatus according to this disclosure further includes a result output section that outputs a determination result from the respiratory phase determination section using a predetermined method.

In the respiratory phase determination apparatus according to this disclosure: the first breath sound is a tracheal breath sound or bronchial breath sound; and the second breath sound is a vesicular breath sound.

A respiratory phase determination method according to this disclosure includes: estimating a respiratory period based on at least one of a first breath sound acquired from a first position of a body of a subject and a second breath sound acquired in synchronization with the first breath sound from a second position of the body of the subject; extracting a first period feature value representing a feature of the first breath sound in the respiratory period; extracting a second period feature value representing a feature of the second breath sound in the respiratory period; relativizing the first period feature value and the second period feature value and calculating a combined feature value; and comparing the combined feature value in the respiratory period with a combined feature value in a respiratory period near the respiratory period and determining whether each of the two respiratory periods is an inspiratory phase or expiratory phase based on a comparison result and a predetermined datum.

A respiratory phase determination program according to this disclosure is a program that causes a computer to execute processing comprising: estimating a respiratory period based on at least one of a first breath sound acquired from a first position of a body of a subject and a second breath sound acquired in synchronization with the first breath sound from a second position of the body of the subject; extracting a first period feature value representing a feature of the first breath sound in the respiratory period; extracting a second period feature value representing a feature of the second breath sound in the respiratory period; relativizing the first period feature value and the second period feature value and calculating a combined feature value; and comparing the combined feature value in the respiratory period with a combined feature value in a respiratory period near the respiratory period and determining whether each of the two respiratory periods is an inspiratory phase or expiratory phase based on a comparison result and a predetermined datum.

The disclosure of Japanese Patent Application No. 2012-287619, filed on Dec. 28, 2012, including the specification, drawings, and abstract, is incorporated herein by reference in its entirety.

INDUSTRIAL APPLICABILITY

The respiratory phase determination apparatus, respiratory phase determination method, and respiratory phase determination program according to the present invention are useful for an apparatus, method, and program or the like for determining a respiratory phase based on breath sounds. The present invention is also applicable to control over CG (computer graphics) linked to a respiratory phase or the like.

REFERENCE SIGNS LIST

101 First sensor
102 First breath sound extraction section
103 Second sensor
104 Second breath sound extraction section
105 Respiratory period estimation section
106 First period feature value extraction section
107 Second period feature value extraction section
108 Feature value relativization/combining section
109 Respiratory phase determination section
110 Result output section

The invention claimed is:

1. A respiratory phase determination apparatus, which compensates for differences in respiration among subjects or variations in respiration of a subject without calibration, the respiratory phase determination apparatus comprising
a first sensor that is attached at a first position of a body of a subject to acquire a first biological sound signal including a first breath sound signal, the first breath sound signal has a usual power of an inspiratory phase greater than a usual power of an expiratory phase;
a second sensor that is attached at a second position of the body of the subject to acquire a second biological sound signal including a second breath sound signal, the second breath sound signal has a usual power of an inspiratory phase smaller than a usual power of an expiratory phase; and
circuitry operative to:
receive the first breath sound signal from the first sensor and the second breath sound signal from the second sensor during a first predetermined time;
calculate a first power of the first breath sound signal for each of a plurality of time frames and a second power of the second breath sound signal for each of the time frames, the first predetermined time being divided into the plurality of time frames;
extract pauses, each of the pauses including consecutive time frames in which either one of the first power is less than a first threshold value and the second power is less than a second threshold value;
extract respiratory periods, each of the respiratory periods between one pause of the extracted pauses and next one pause of the extracted pauses, the one pause and the next one pause are temporally located next to each other in the extracted pauses and being longer than a second predetermined time;
determine a first average power of the first breath sound signal, by using the first power, in each of the respiratory periods and a second average power of the second breath sound signal, by using the second power, in each of the respiratory periods;
obtain a combined average power by subtracting the first average power from the second feature value for each of the respiratory periods, the combined average power cancelling fluctuations due to irregularity in the first breath sound signal and the second breath sound signal;
compare two of the combined average powers obtained for a pair of respiratory periods to determine which one of the two combined average powers is larger, the pair of respiratory periods including two consecutive respiratory periods;
determine whether a previous period included in the pair of respiratory periods and a following period in the pair of respiratory periods correspond to an inspiratory phase or expiratory phase based on a result of the comparison and a predetermined datum; and
output a result of the determination, to perform a lung sound analysis for an asthma test on the first or second biological sound signal at least in the determined inspiratory phase,
wherein
the first position is set to acquire a vesicular breath in a first predetermined range of the body of the subject,
the second position is set to acquire a tracheal breath sound or bronchial breath sound in a second predetermined range of the body of the subject,
the predetermined datum indicates that one respiratory period in the pair of respiratory periods which has larger combined average power corresponds to the expiratory phase and the other respiratory period in the pair of respiratory periods corresponds to the inspiratory phase.

2. The respiratory phase determination apparatus according to claim 1, wherein the circuitry is further operative to adopt a result of the determination with which inspiratory phases and expiratory phases appear alternately in a series of respiratory periods or adopt a result of the determination which has a greater difference from the datum, when two results of the determination for one respiratory period are obtained, and are in conflict with each other, and wherein the one respiratory period is regarded as the previous period in one of the two results and the one respiratory period is regarded as the following period in the other one of the two results.

3. The respiratory phase determination apparatus according to claim 1,
wherein the circuitry is further operative to remove a cardiac sound or noise in a high-frequency region from the first biological sound signal and the second biological sound signal using a band-pass filter, to extract the first breath sound signal from the first biological sound signal and the second breath sound signal from the second biological sound signal.

4. A respiratory phase determination method, which compensates for personal differences in respiration among subjects or variations in respiration of a subject without calibration, the respiratory phase determination method comprising:
receiving a first breath sound signal from a first sensor and a second breath sound signal from a second sensor during a first predetermined time, wherein the first breath sound signal is acquired from a first position of a body of a subject and the second breath sound signal is acquired in synchronization with the first breath sound signal from a second position of the body of the subject, the first breath sound signal has a usual power of an inspiratory phase greater than a usual power of an expiratory phase, and the second breath sound signal has a usual power of an inspiratory phase smaller than a usual power of an expiratory phase;
calculating a first power of the first breath sound signal for each of a plurality of time frames and a second power of the second breath sound signal for each of the plurality of time frames, the first predetermined time being divided into the time frames;
extracting pauses, each of the pauses including consecutive time frames in which either one of the first power is less than a first threshold value and the second power is less than a second threshold value;
extracting respiratory periods, each of the respiratory periods between one pause of the extracted pauses and next one pause of the extracted pauses, the one pause and the next one pause are temporally located next to each other in the extracted pauses and being longer than a second predetermined time;
determining a first average power of the first breath sound signal, by using the first power, in each of the respiratory periods and a second average power of the second breath sound signal, by using the second power, in each of the respiratory periods;
cancelling fluctuations due to irregularity in the first breath sound signal and the second breath sound signal by obtaining a combined average power by subtracting the first average power from the second average power for each of the respiratory periods;
comparing two of the combined average powers obtained for a pair of respiratory periods to determine which one of the two combined average powers is larger, the pair of respiratory periods including two consecutive respiratory periods;
determining whether a previous period included in the pair of respiratory periods and a following period in the pair of respiratory periods correspond to an inspiratory phase or expiratory phase based on a result of the comparison and a predetermined datum; and outputting a result of the determination, to perform a lung sound analysis for an asthma test on the first or second biological sound signal at least in the determined inspiratory phase,
wherein
the first position is set to acquire a vesicular breath in a first predetermined range of the body of the subject,
the second position is set to acquire a tracheal breath sound or bronchial breath sound in a second predetermined range of the body of the subject,
the predetermined datum indicates that one respiratory period in the pair of respiratory periods which has larger combined average power corresponds to the expiratory phase and the other respiratory period in the pair of respiratory periods corresponds to the inspiratory phase.

5. A respiratory phase determination program recorded on a non-transitory computer-readable recording medium that causes a computer to execute processing, which compensates for differences in respiration among subjects or variations in respiration of a subject without calibration, the processing comprising:
receiving a first breath sound signal from a first sensor and a second breath sound signal from a second sensor during a first predetermined time, wherein the first breath sound signal is acquired from a first position of a body of a subject and the second breath sound signal is acquired in synchronization with the first breath sound signal from a second position of the body of the subject, the first breath sound signal has a usual power of an inspiratory phase greater than a usual power of an expiratory phase, and the second breath sound signal has a usual power of an inspiratory phase smaller than a usual power of an expiratory phase;
calculating a first power of the first breath sound signal for each of a plurality of time frames and a second power of the second breath sound signal for each of the time frames, the first predetermined time being divided into the plurality of time frames;
extracting pauses, each of the pauses including consecutive time frames in which either one of the first power is less than a first threshold value and the second power is less than a second threshold value;
extracting respiratory periods, each of the respiratory periods between one pause of the extracted pauses and next one pause of the extracted pauses, the one pause and the next one pause are temporally located next to each other in the extracted pauses and being longer than a second predetermined time;
determining a first average power of the first breath sound signal, by using the first power, in each of the respiratory periods and a second average power of the second breath sound signal, by using the second power, in each of the respiratory periods;
cancelling fluctuations due to irregularity in the first breath sound signal and the second breath sound signal by obtaining a combined average power by subtracting the first average power from the second average power for each of the respiratory periods;
comparing two of the combined average powers obtained for a pair of respiratory periods to determine which one of the two combined average powers is larger, the pair of respiratory periods including two consecutive respiratory periods;
determining whether a previous period included in the pair of respiratory periods and a following period in the pair of respiratory periods correspond to an inspiratory phase or expiratory phase based on a result of the comparison and a predetermined datum; and outputting a result of the determination, to perform a lung sound analysis for an asthma test on the first or second biological sound signal at least in the determined inspiratory phase, wherein the first position is set to acquire a vesicular breath in a first predetermined range of the body of the subject, the second position is set to acquire a tracheal breath sound or bronchial breath sound in a second predetermined range of the body of the subject, the predetermined datum indicates that one respiratory period in the pair of respiratory periods which has larger combined average power corresponds to the expiratory phase and the other respiratory period in the pair of respiratory periods corresponds to the inspiratory phase.

6. A respiratory phase determination apparatus, which compensates for differences in respiration among subjects or variations in respiration of a subject without calibration, the respiratory phase determination apparatus comprising a first sensor that is attached at a first position of a body of a subject to acquire a first biological sound signal including a first breath sound signal, the first breath sound signal has a usual power of an inspiratory phase greater than a usual power of an expiratory phase;

a second sensor that is attached at a second position of the body of the subject to acquire a second biological sound signal including a second breath sound signal, the second breath sound signal has a usual power of an inspiratory phase smaller than a usual power of an expiratory phase; and circuitry operative to:

receive the first breath sound signal from the first sensor and the second breath sound signal from the second sensor during a first predetermined time;

calculate a first power of the first breath sound signal for each of a plurality of time frames and a second power of the second breath sound signal for each of the time frames, the first predetermined time being divided into the plurality of time frames;

extract pauses, each of the pauses including consecutive time frames in which either one of the first power is less than a first threshold value and the second power is less than a second threshold value;

extract respiratory periods, each of the respiratory periods between one pause of the extracted pauses and next one pause of the extracted pauses, the one pause and the next one pause are temporally located next to each other in the extracted pauses and being longer than a second predetermined time;

determine a first average power of the first breath sound signal, by using the first power, in each of the respiratory periods and a second average power of the second breath sound signal, by using the second power, in each of the respiratory periods;

obtain a combined average power by subtracting the first average power from the second average power for each of the respiratory periods, the combined average power cancelling fluctuations due to irregularity in the first breath sound signal and the second breath sound signal;

compare two of the combined average powers obtained for a pair of respiratory periods to determine which one of the two combined average powers is larger, the pair of respiratory periods including two consecutive respiratory periods;

determine whether a previous period included in the pair of respiratory periods and a following period in the pair of respiratory periods correspond to an inspiratory phase or expiratory phase based on a result of the comparison and a predetermined datum; and output a result of the determination, to perform a lung sound analysis for an asthma test on the first or second biological sound signal at least in the determined inspiratory phase, the first breath sound signal is a vesicular breath sound signal and the second breath sound signal is a tracheal breath sound signal or bronchial breath sound signal, and the predetermined datum indicates that one respiratory period in the pair of respiratory periods which has larger combined average power corresponds to the expiratory phase and the other respiratory period in the pair of respiratory periods corresponds to the inspiratory phase.

7. A respiratory phase determination method which compensates for differences in respiration among subjects or variations in respiration of a subject without calibration, the respiratory phase determination method comprising:

receiving a first breath sound signal from a first sensor and a second breath sound signal from a second sensor during a first predetermined time, wherein the first breath sound signal is acquired from a first position of a body of a subject and the second breath sound signal is acquired in synchronization with the first breath sound signal from a second position of the body of the subject, the first breath sound signal has a usual power of an inspiratory phase greater than a usual power of an expiratory phase, and the second breath sound signal has a usual power of an inspiratory phase smaller than a usual power of an expiratory phase;

calculating a first power of the first breath sound signal for each of a plurality of time frames and a second power of the second breath sound signal for each of the time frames, the first predetermined time being divided into the plurality of time frames;

extracting pauses, each of the pauses including consecutive time frames in which either one of the first power is less than a first threshold value and the second power is less than a second threshold value;

extracting respiratory periods, each of the respiratory periods between one pause of the extracted pauses and next one pause of the extracted pauses, the one pause and the next one pause are temporally located next to each other in the extracted pauses and being longer than a second predetermined time;

determining a first average power of the first breath sound signal, by using the first power, in each of the respiratory periods and a second average power of the second breath sound signal, by using the second power, in each of the respiratory periods;

cancelling fluctuations due to irregularity in the first breath sound signal and the second breath sound signal by obtaining a combined average power by subtracting the first average power from the second average power for each of the respiratory periods;

comparing two of the combined average powers obtained for a pair of respiratory periods to determine which one of the two combined average powers is larger, the pair of respiratory periods including two consecutive respiratory periods;

determining whether a previous period included in the pair of respiratory periods and a following period in the pair of respiratory periods correspond to an inspiratory phase or expiratory phase based on a result of the comparison and a predetermined datum; and outputting a result of the determination, to perform a lung sound analysis for an asthma test on the first or second biological sound signal at least in the determined inspiratory phase, wherein the first breath sound signal is a vesicular breath sound signal and the second breath sound signal is a tracheal breath sound signal or bronchial breath sound signal, and the predetermined datum indicates that one respiratory period in the pair of respiratory periods which has larger combined average power corresponds to the expiratory phase and the other respiratory period in the pair of respiratory periods corresponds to the inspiratory phase.

8. A respiratory phase determination program recorded on a non-transitory computer-readable recording medium that causes a computer to execute processing, which compensates for differences in respiration among subjects or variations in respiration of a subject without calibration, the processing comprising:

receiving a first breath sound signal from a first sensor and a second breath sound signal from a second sensor during a first predetermined time, wherein the first breath sound signal is acquired from a first position of a body of a subject and the second breath sound signal is acquired in synchronization with the first breath sound signal from a second position of the body of the subject, the first breath sound signal has a usual power of an inspiratory phase greater than a usual power of an expiratory phase, and the second breath sound signal has a usual power of an inspiratory phase smaller than a usual power of an expiratory phase;

calculating a first power of the first breath sound signal for each of a plurality of time frames and a second power of the second breath sound signal for each of the time frames, the first predetermined time being divided into the plurality of time frames;

extracting pauses, each of the pauses including consecutive time frames in which either one of the first power is less than a first threshold value and the second power is less than a second threshold value;

extracting respiratory periods, each of the respiratory periods between one pause of the extracted pauses and next one pause of the extracted pauses, the one pause and the next one pause are temporally located next to each other in the extracted pauses and being longer than a second predetermined time;

determining a first average power of the first breath sound signal, by using the first power, in each of the respiratory periods and a second average power of the second breath sound signal, by using the second power, in each of the respiratory periods;

cancelling fluctuations due to irregularity in the first breath sound signal and the second breath sound signal by obtaining a combined average power by subtracting the first average power from the second average power for each of the respiratory periods;

comparing two of the combined average powers obtained for a pair of respiratory periods to determine which one of the two combined average powers is larger, the pair of respiratory periods including two consecutive respiratory periods;

determining whether a previous period included in the pair of respiratory periods and a following period in the pair of respiratory periods correspond to an inspiratory phase or expiratory phase based on a result of the comparison and a predetermined datum; and outputting a result of the determination, to perform a lung sound analysis for an asthma test on the first or second biological sound signal at least in the determined inspiratory phase, wherein the first breath sound signal is a vesicular breath sound signal and the second breath sound signal is a tracheal breath sound signal or bronchial breath sound signal, and the predetermined datum indicates that one respiratory period in the pair of respiratory periods which has larger combined average power corresponds to the expiratory phase and the other respiratory period in the pair of respiratory periods corresponds to the inspiratory phase.

* * * * *